United States Patent
Bauer et al.

(10) Patent No.: US 8,311,746 B2
(45) Date of Patent: Nov. 13, 2012

(54) METHODS FOR PREDICTING FATTY ACID ENRICHMENT

(75) Inventors: John E. Bauer, College Station, TX (US); Mark K. Waldron, St. Louis, MO (US)

(73) Assignee: Nestec S.A., Vevey (CH)

( * ) Notice: Subject to any disclaimer, the term of this patent is extended or adjusted under 35 U.S.C. 154(b) by 948 days.

(21) Appl. No.: 10/513,550

(22) PCT Filed: May 5, 2003

(86) PCT No.: PCT/EP03/04902

§ 371 (c)(1),
(2), (4) Date: Nov. 4, 2004

(87) PCT Pub. No.: WO03/092405

PCT Pub. Date: Nov. 13, 2003

(65) Prior Publication Data

US 2006/0167635 A1 Jul. 27, 2006

Related U.S. Application Data

(60) Provisional application No. 60/378,280, filed on May 6, 2002.

(51) Int. Cl.
*G01N 33/48* (2006.01)
*G06G 7/48* (2006.01)

(52) U.S. Cl. ............................................ 702/19; 703/11
(58) Field of Classification Search .................. None
See application file for complete search history.

(56) References Cited

OTHER PUBLICATIONS

Hall et al., "The (n-3) Fatty ACid Dose, Independent of the (n-6) and (n-3) Fatty acid ratio, Affects the Plasma Fatty Acid Profile of Normal Dogs", The Journal of Nutrition (2006) vol. 136, pp. 2338-2344.*
Lands et al. "Maintenance of lower porportions of 9n-60 eicosanoid precursors in phospholipids of human plasma in response to added dietary (n-3) fatty acids" Biochim Biophys Acta (Dec. 10, 1992) vol. 1180(2): Abstract only.*

* cited by examiner

*Primary Examiner* — Eric S Dejong
(74) *Attorney, Agent, or Firm* — K&L Gates LLP

(57) ABSTRACT

Methods and equations are provided for predicting the enrichment of polyunsaturated fatty acids in a canine based on a known diet. The methods and equations of the present invention can be used to predict the enrichment of linoleic acid and α-linolenic acid in plasma triglycerides and n-3 and n-6 type highly unsaturated fatty acids in plasma phospholipids and neutrophil phospholipids. The ability to accurately predict the enrichment of polyunsaturated fatty acids in a canine based on diet may be used to design specific diets to meet certain dietary needs.

15 Claims, 4 Drawing Sheets

PREDICTED MAINTENANCE OF FATTY ACIDS IN PLASMA LIPIDS

| | Diet Identifier>> | jbsunf | jbflax | 40-BTO | 40-SFO | 40-LSO | 40-MHO | 20-SFO | 20-BTO |
|---|---|---|---|---|---|---|---|---|---|
| CONSTANTS | AVERAGE DAILY DIETARY INTAKES | | | | | | | | |
| Vmax= 100.0 | en%3 | 0.4 | 2.27 | 0.32 | 0.27 | 19.585 | 0.432 | 0.26 | 0.28 |
| PC6= 0.0360 | en%6 | 9.3 | 7.3 | 3.107 | 27.404 | 7.604 | 2.488 | 12.72 | 2.847 |
| PC3= 0.2900 | en%H3 | 0.000001 | 0.000001 | 0.000001 | 0.000001 | 0.000001 | 8.728 | 0.000001 | 0.000001 |
| C0= 9.00 | en%H6 | 0.09 | 0.09 | 0.003 | 0.035 | 0.003 | 0.422 | 0.035 | 0.022 |
| Ks= 0.140 | en%0 | 13.26 | 13.56 | 36 | 12.91 | 13.63 | 24.26 | 7.4 | 16.85 |
| HI6= 0.010 | PLASMA PL: PREDICTED HUFA | | | | | | | | |
| HI3= 0.100 | 20:5+22:5n-3 (as % of HUFA in PL) | | | | | | | | |
| HC6= 4.0 | Using Eq.#3 | 4.8 | 17.1 | 8.5 | 2.0 | 30.6 | 44.5 | 3.5 | 8.1 |
| HC3= 11.0 | 20:3+20:4n-6 (as % of HUFA in PL) | | | | | | | | |
| | Using Eq.#4 | 80.9 | 79.0 | 75.5 | 80.1 | 64.9 | 44.1 | 80.0 | 77.2 |
| factor3 1.31 | Other HUFA (as % of HUFA in PL) | | | | | | | | |
| factor6 2.98 | 22:6n3; 20:3n9 | 14.3 | 3.9 | 16.0 | 17.9 | 4.5 | 11.3 | 16.6 | 14.7 |
| | PLASMA TG: PREDICTED UFA | | | | | | | | |
| KI3 0.34 | 18:3n-3 (as wt% in TG) | | | | | | | | |
| KI6 0.72 | Using factor 3 linear | 0.5 | 3.0 | 0.4 | 0.4 | 25.7 | 0.6 | 0.3 | 0.4 |
| | 18:2n-6 (as wt% in TG) | | | | | | | | |
| | Using factor 6 linear | 27.7 | 21.8 | 9.3 | 81.7 | 22.7 | 7.4 | 37.9 | 8.5 |
| 18:2 constants | | | | | | | | | |
| a= -0.06 | Using Equation 1 | 24.4 | 20.9 | 12.0 | 34.3 | 21.5 | 10.5 | 29.3 | 11.4 |
| b= 2.8 | | | | | | | | | |
| c= 4.0 | Using Equation 2 | 0.5 | 2.5 | 0.4 | 0.3 | 17.2 | 0.5 | 0.3 | 0.3 |
| 18:3 constants | | | | | | | | | |
| a= -0.012 | | | | | | | | | |
| b= 1.110 | | | | | | | | | |
| c= 0.020 | | | | | | | | | |

Fig. 1

PREDICTED MAINTENANCE OF FATTY ACIDS IN NEUTROPHILS

| CONSTANTS | | Diet Identifier>> | jbsunf | jbflax | 40-BTO | 40-SFO | 40-LSO | 40-MHO | 20-SFO | 20-BTO |
|---|---|---|---|---|---|---|---|---|---|---|
| | | AVERAGE DAILY DIETARY INTAKES | | | | | | | | |
| Vmax= | 100.0 | en%3 | 0.4 | 2.27 | 0.32 | 0.27 | 19.585 | 0.432 | 0.26 | 0.28 |
| PC6= | 0.0360 | en%6 | 9.3 | 7.3 | 3.107 | 27.404 | 7.604 | 2.488 | 12.72 | 2.847 |
| PC3= | 0.2900 | en%H3 | 0.000001 | 0.000001 | 0.000001 | 0.000001 | 0.000001 | 8.728 | 0.000001 | 0.000001 |
| C0= | 9.00 | en%H6 | 0.09 | 0.09 | 0.003 | 0.035 | 0.003 | 0.422 | 0.035 | 0.022 |
| Ks= | 0.140 | en%O | 13.26 | 13.56 | 36 | 12.91 | 13.63 | 24.26 | 7.4 | 16.85 |
| | | NEUTROPHIL PL: PREDICTED HUFA | | | | | | | | |
| HI6= | 0.010 | 20:5+22:5n-3 (as % of HUFA in PL) | | | | | | | | |
| HI3= | 0.100 | | | | | | | | | |
| HC6= | 4.0 | Using Eq.#3 | 0.5 | 3.1 | 1.1 | 0.1 | 15.6 | 43.0 | 0.2 | 8.1 |
| HC3= | 11.0 | 20:3+20:4n-6 (as % of HUFA in PL) | | | | | | | | |
| | | Using Eq.#4 | 81.0 | 80.1 | 75.8 | 80.2 | 72.3 | 44.3 | 80.0 | 77.2 |
| KI3 | 0.8 | Other HUFA (as % of HUFA in PL) | 18.5 | 16.8 | 23.0 | 19.7 | 12.2 | 12.7 | 19.7 | 14.7 |
| KI6 | 0.034 | 22:6n3; 20:3n9 | | | | | | | | |

Fig. 2

METHODS FOR PREDICTING FATTY ACID ENRICHMENT

FIELD OF THE INVENTION

The present invention relates to methods for predicting the fatty acid enrichment of canine plasma and neutrophils resulting when a specific diet of known composition is fed to a canine. More specifically, the present invention relates to methods for predicting the enrichment of highly unsaturated fatty acids in canine plasma and neutrophils based on the amount of fatty acids in the canine diet. The methods allow for more precise formulation of canine food products.

BACKGROUND OF THE INVENTION

Polyunsaturated fatty acids of the n-3 or n-6 type are not synthesized de novo in animal tissue. Although polyunsaturated fatty acids can be synthesized by the elongation and desaturation enzymes of animal tissue, the n-3 or n-6 type of structures can only be obtained from dietary sources. The presence and amounts of the n-3 or n-6 type polyunsaturated fatty acids in animal tissue reflects the origin of these two types of fatty acids in plant tissues used as sources of food. The essential polyunsaturated fatty acids usually found in plant tissue include linoleic acid (18:2n-6) and α-linolenic acid (18:3n-3). When an animal is fed with a source of n-3 or n-6 polyunsaturated fatty acids, displacement of endogenous fatty acids (20:3n9 and 20:4n-7 types) occurs, resulting in the enrichment of n-3 and n-6 highly unsaturated fatty acids (HUFA), specifically 20:4n-6, 20:5n-3, 22:5n-3, 22:6n-3. Because the precursors of the n-3 and n-6 HUFAs can only be obtained from dietary sources, their relative abundance in tissues is limited by the availability of these precursors in the diet.

The 20-carbon HUFAs play important roles as substrates and antagonists of eicosanoid biosynthesis. Altering the abundance of dietary precursors of these HUFAs may influence a tissue's capacity to form specific eicosanoids. An altered capacity in turn may affect the frequency and severity of eicosanoid-related disorders, such as cardiovascular disease and osteo and rheumatoid arthritis. It is also known that optimizing the enrichment of these HUFAs can be used to treat or affect a variety of conditions, including but not limited to, inflammatory, developmental, renal, dermatological, and blood pressure related conditions.

Thus, it would be desirable to have a method to predict the enrichment of n-3 and n-6 type HUFAs in plasma and cells of canines based on the amount of polyunsaturated fatty acids (PUFA) in the diets. It would further be desirable if the method could determine the enrichment of n-6 and n-3 type PUFAs in the triglycerides (TG) or HUFAs in the phospholipids (PL) formed in plasma or neutrophils. Formulae have been developed for predicting n-3 and n-6 type HUFA in Humans, Lands, W. E. M. et al., *Biochem. Biophys. Acta,* 1180, 147-162 (1992), and in rats, Lands, W. E. M. et al., *Lipids,* 25, 505-516 (1990). However, no such formulae have been previously available for predicting n-3 and n-6 type HUFA in canines. Without such equations, effectiveness of a proposed diet formulation would be tested by feeding the proposed diet to a group of dogs for a period of time, perhaps 3-4 weeks or more, and subsequently measuring the plasma and neutrophil levels of fatty acids and levels of enrichment. If the measurements indicated that adjustments to the proposed diet were necessary, the adjusted proposed diet similarly may be fed to a group of dogs, to determine if the proper levels were reached. Thus, it could take weeks or months to determine if the desired fatty acid levels would be reached using a proposed diet formulation.

SUMMARY OF THE INVENTION

Methods are provided in the present invention for predicting the enrichment of the n-3 and n-6 type of highly unsaturated fatty acids (HUFAs) in a canine based on the content of n-6 and n-3 polyunsaturated fatty acids (PUFAs) in the canine's diet. HUFAs are defined as highly unsaturated fatty acids having at least 20 carbons, and preferably 20 or 22 carbons, with two or more double bonds. Methods are also provided for predicting the enrichment of linoleic acid and a-linolenic acid in the plasma. The methods of the present invention comprise providing a diet having known amounts of linoleic acid (LA), α-linolenic acid (ALA), n-6 HUFA and n-3 HUFA, and calculating the predicted enrichment of n-3 and n-6 type HUFA in the canine using novel equations. The methods of the present invention may further comprise formulating a new diet or adjusting an existing canine diet based on the results of the predicted values to provide optimal n-3 and n-6 HUFA enrichment for specific medical or developmental needs.

The present invention further provides methods using novel equations and constants for calculation of the enrichment of n-3 and n-6 type HUFAs in a canine based on a known diet. In one embodiment, the equation for predicting the amount of LA (18: 2n-6) enrichment in plasma triglycerides is $y=-0.62x^2+2.75x+4.04$, in which y is the amount of enrichment and x is a variable, en%6. The variable en % 6 is determined from the diet and is the percent of daily energy or calories provided by LA in the diet. In an alternative embodiment, the equation for predicting the amount of ALA (18:3n-3) in plasma triglycerides is $y=-0.012x^2+1.11x+0.02$, in which y is the predicted amount of ALA in the triglyceride fraction and x is en % 3, the percent of daily energy attributed to ALA in a diet.

In yet another embodiment methods are provided for predicting the enrichment of n-6 and n-3 HUFAs in the phospholipids of canine plasma and neutrophils using novel equations. The equations employ the percentage of daily energy or calories contributed by LA, ALA, n-3 and n-6 HUFAs, and other fats, the rate of conversion of the fatty acids from their dietary form into the canine phospholipids, and the competition of conversion between the n-3 and n-6 unsaturated fatty acids. The constants required for the equations of the present invention have been determined experimentally and are specific for canine plasma or neutrophils.

The methods and equations of the present invention may be used to formulate specific canine diets to provide healthy levels of n-3 and n-6 HUFAs in a canine. Diets can be formulated for general populations taking into account factors such as, but not limited to, age, weight, and health. Alternatively, a diet may be formulated by a veterinarian for a specific canine animal with health problems or potential health problems using the methods and equations of the present invention. Conversely, the amount of n-3 and n-6 HUFAs in a specific canine can be calculated based on the canine's diet without requiring costly and time consuming sample analysis.

Additional objects, advantages and features of the present invention will become apparent from the following description and appended claims, taken in conjunction with the accompanying drawing.

BRIEF DESCRIPTION OF THE DRAWINGS

The various advantages of the present invention will become apparent to one skilled in the art by reading the following specification and subjoined claims and by referring to the following drawing in which:

FIG. 1 is a chart showing predicted phospholipid and triglyceride levels in plasma for various diets.

FIG. 2 is similar to FIG. 1, except showing the predicted phospholipid levels in neutrophils.

DETAILED DESCRIPTION OF THE PREFERRED EMBODIMENT

Figure 3:
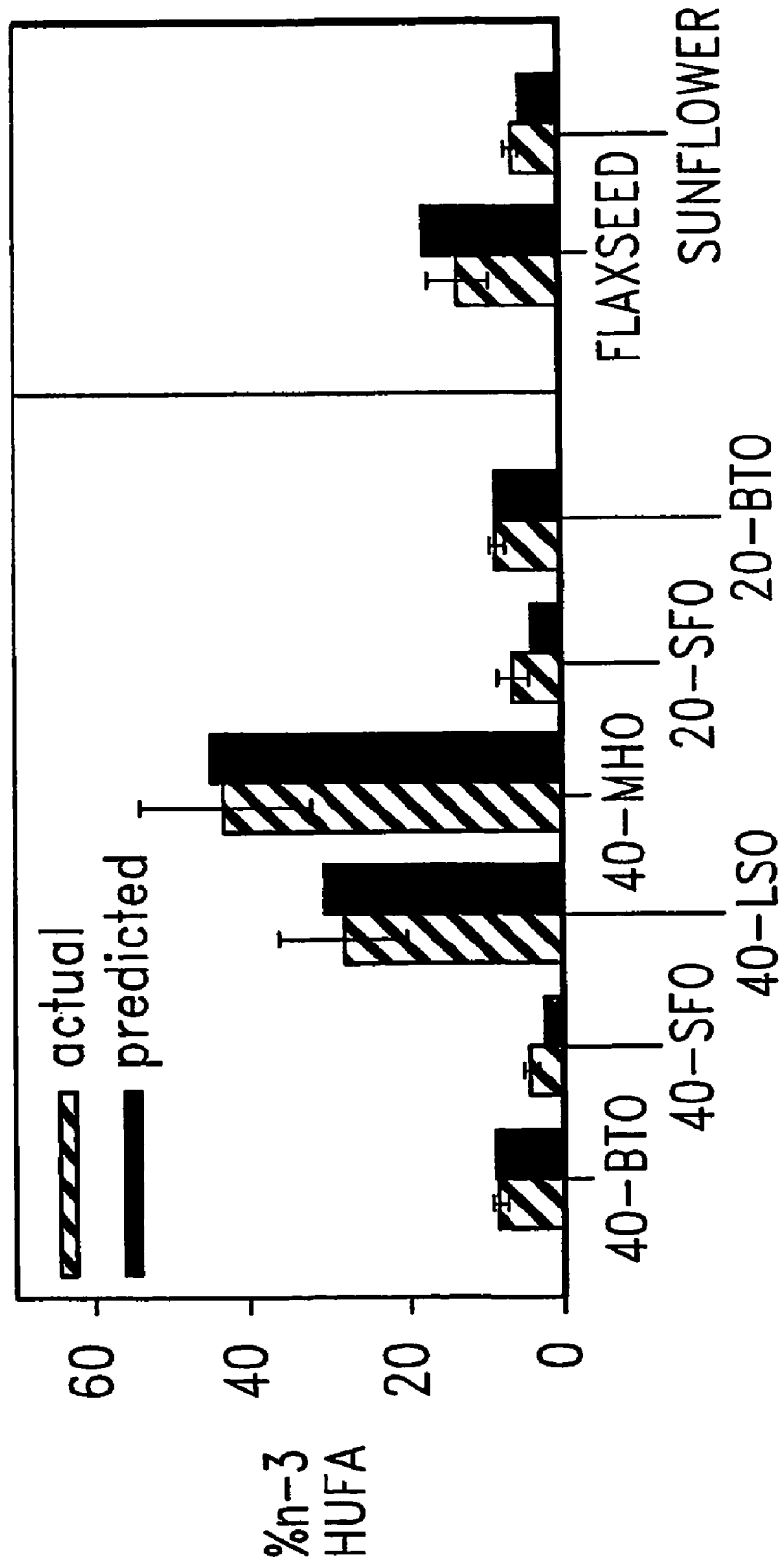
FIG. 3 is a bar graph comparing the predicted and actual values of n-3 HUFA enrichment in canine plasma. The black bars indicate the predicted values, while the white bars indicate the actual values.

Methods are provided for predicting the enrichment of n-3 and n-6 polyunsaturated fatty acids in the triglycerides and HUFAs in the phospholipids of a canine based on the fat content and composition of a specific canine diet. Methods are also provided for formulating specific canine diets based on the predicted enrichment. In one embodiment, a method of the present invention comprises selecting a diet, determining the percentage of caloric energy contribution from fats in the diet, and calculating the predicted enrichment of n-3 and n-6 HUFA in triglycerides and phospholipids in the canine. The method may further comprise adjusting the fat make-up of the diet to adjust the amount of n-3 and n-6 HUFA enrichment. In an illustrated embodiment the enrichment is predicted for plasma triglycerides and plasma and neutrophil phospholipids. The methods of the present invention may be used to formulate canine diets for specific populations of animals to provide healthy levels of n-3 and n-6 HUFA enrichment. Canine diets can be formulated for populations based on, but not limited to, age, weight, and health. Alternatively, the methods of the present invention can be used to formulate a diet for a specific canine animal. It would be desirable to have such a diet for an animal with, by way of non-limiting example, rheumatoid arthritis. The exact amount of n-3 and n-6 HUFA enrichment will very from situation to situation and can easily be determined by the skilled artisan.

The present invention also provides methods using novel equations and constants for calculating the predicted enrichment of n-3 and n-6 HUFAs, particularly LA and ALA in triglycerides and phospholipids. To develop the equations, previously published work in rats was reviewed and new constants were developed for canines. To develop these values, clinically normal adult dogs were fed known basal diets plus beef tallow, safflower oil, linseed oil, or menhaden fish oil (40 en % fat), or plus beef tallow or safflower oil (20 en % fat). Plasma was collected on Day 0 and plasma and whole blood were collected on Day 28 during the supplement period. Neutrophils were isolated via gradient centrifugation. Total lipids were extracted and lipid classes subfractionated via thin layer chromatography. Lipid subfractions (total phospholipid in plasma and neutrophils and triglyceride in plasma) were derivatized to fatty acid methyl esters and gas chromatography used to generate fatty acid profiles. The 18:2n-6 and 18:3n-3 triglyceride fatty acids were expressed as weight % while the phospholipid fatty acid results were expressed as n-6 and n-3 HUFA as a percentage of total HUFA. Dietary n-3 and n-6 fatty acids ranged from 0.26-19.6 for 18:3n-3; 2.5-27.4 for 18:2n-6; 0.0-8.8 for n-3 HUFA; and 0.0-0.09 for n-6 HUFA (all en %). Algebraic equations resembling the competitive hyperbolic relationship commonly used to describe rate-limiting processes (see Lands, W. E. M. et al., *Biochem. Biophys. Acta,* 1180, 147-162 (1992)) were modified to fit the canine phospholipid data and second-order polynomial regression analysis was used to fit the plasma triglyceride data. Regression of the triglyceride data revealed $r^2$ values of 0.999 and 0.997 at $p<0.05$ for the 18:3n-3 and 18:2n-6 acids respectively, allowing accurate prediction of plasma triglyceride fatty acids from known dietary amounts. Constants for the phospholipid hyperbolic equations were determined using those developed in other species using trial and error modifications.

In one embodiment methods using equations for determining the enrichment of LA or ALA in plasma triglycerides are provided. In an illustrated embodiment, predicted enrichment of LA (18:2n-6) is calculated using Equation 1:

$$y = -0.62x^2 + 2.75x + 4.04 \quad (1)$$

wherein y is the weight percent of LA enrichment and x is the percentage of daily caloric energy attributed to LA in a diet (en % 6). In an alternative embodiment, the predicted enrichment of ALA (18:3n-3) in plasma triglycerides is calculated using Equation 2:

$$y = -0.012x^2 + 1.11x + 0.02 \quad (2)$$

wherein y is the weight percent of ALA enrichment and x is the percentage of daily caloric energy attributed to ALA in a diet (en % 3).

The equations of the present invention for predicting enrichment of LA or ALA in plasma triglycerides are quadratic equations. The constants were determined by fitting actual values measured for triglyceride enrichment. Equations for plasma triglyceride levels in rat and human were previously developed. However, while the present equations are quadratic equations, the prior rat and human equations are linear equations using different constants. Lands, W. E. M. et al., *Lipids,* 25, 505-516 (1990); Lands, W. E. M. et al., *Biochem. Biophys. Acta* 1180, 147-162 (1992). A comparison of the linear equations of Lands and the quadratic equations of the present invention is shown in FIG. 1. The linear equations are y=x(factor3) and y=x(factor6), respectively. As is shown in FIG. 1, the Lands equations (Using Factor3 and Using Factor6) and Equations 1 and 2 result in very different predicted triglyceride values.

In another embodiment equations are provided for calculating the predicted phospholipid HUFAs in plasma or neutrophils. In an illustrated embodiment, the predicted enrichment of n-3 HUFA is calculated using Equation 3 and the predicted enrichment of n-6 HUFA is calculated using Equation 4:

$$\% \ (n\text{-}3)HUFA = \frac{100}{1 + \{(PC_3/en\%3)[1 + (en\%6/KI_6) + (en\%H_6/HI_6) + (en\%O/C_o) + (en\%3/K_5)]\}} + \frac{100}{1 + \{(HC_3/en\%H_3)[1 + (en\%H_6/HC_6)]\}}, \quad (3)$$

$$\% \ (n\text{-}6)HUFA = \frac{100}{1 + \{(PC_6/en\%6)[1 + (en\%3/KI_3) + (en\%H_3/HI_3) + (en\%O/C_o) + (en\%6/K_5)]\}} + \frac{100}{1 + \{(HC_6/en\%H_6)[1 + (en\%H_3/HC_3)]\}}, \quad (4)$$

wherein en % 3, en % 6, en % O, en % H6 and en % $H_3$ are the percent daily energy of ALA, LA, other (i.e. saturated and monounsaturated fatty acids), n-6 HUFA, and n-3 HUFA, respectively, in the diet. These values are specific to each individual diet. The energy variables are calculated based on percent of caloric daily energy of the specific component as compared to the total energy of the diet. It is well known in the art how to calculate the percent caloric energy for components in a diet. $HC_3$, $HC_6$, $C_o$, $K_s$, $HI_3$, $HI_6$, $KI_3$ and $KI_6$ are constants specific for canines. $PC_3$ and $PC_6$ are standard effective concentrations of dietary 18:3(n-3) and 18:2(n-6), expressed as a percent of total calories. Two sets of constants have been derived, one for use in determining plasma phospholipid enrichment and the other for use in determining neutrophil phospholipid enrichment. The constants are shown in Table 1.

TABLE 1

Summary of fitted constants derived from the fatty acid concentration of 40% and 20% fat energy diets for canine plasma and neutrophils using the appropriate phospholipid equations.
Constant (energy %)

|  | $PC_6$ | $PC_3$ | $C_o$ | $K_s$ | $HI_6$ | $HI_3$ | $HC_6$ | $HC_3$ | $KI_6$ | $KI_3$ |
|---|---|---|---|---|---|---|---|---|---|---|
| Plasma | 0.036 | 0.290 | 9.00 | 0.140 | 0.010 | 0.100 | 4.00 | 11.00 | 0.72 | 0.34 |
| Neutrophils | 0.036 | 0.290 | 9.00 | 0.140 | 0.010 | 0.100 | 4.00 | 11.00 | 0.034 | 0.80 |

In the equations shown above, % (n-3) HUFA is equivalent to the sum of 20:5(n-3) plus 22:5(n-3) divided by the total HUFA amount in either the plasma or neutrophils, depending on the constants used. Similarly % (n-6) HUFA is equivalent to 20:3(n-6) plus 20:4(n-6) divided by total HUFA, in either the plasma or neutrophils, again depending on the constants used. $HC_3$ and $HC_6$ are constants for the efficiency of direct esterification of dietary n-3 and n-6 HUFA. $C_o$ and $K_s$ are included to adjust for a small effect of other dietary fatty acids ($C_o$) and for shape fitting ($K_s$), respectively. $HI_3$ and $HI_6$ reflect the competitive inhibition by the dietary HUFA in elongation and desaturation of the n-3 and n-6 dietary HUFA. $KI_3$ and $KI_6$ reflect the competitive inhibition by LA and ALA in elongation and desaturation of the n-3 and n-6 LA and ALA. While the equations of the present invention were modeled after the equations used to predict enrichment in humans, the human equations did not contain constants for $KI_3$ and $KI_6$. Instead, the human equations used a concentration term, rather than an inhibition constant. See Lands, W. E. M. et al., *Biochem. Biophys. Acta*, 1180, 147-162 (1992). It was found that the predicted values for enrichment were closer to the actual values when the inhibition due to LA and ALA was taken into consideration.

It is understood that the equations of the present application may be programmed into a device, such as a computer or calculator, wherein the dietary values are inputted into the device, and TG and PL values are provided to the user. Various data input devices, processing units, and displays are known in the art. Alternatively, one may use the equations to calculate the values manually, with or without the aid of a calculator.

Figure 4:
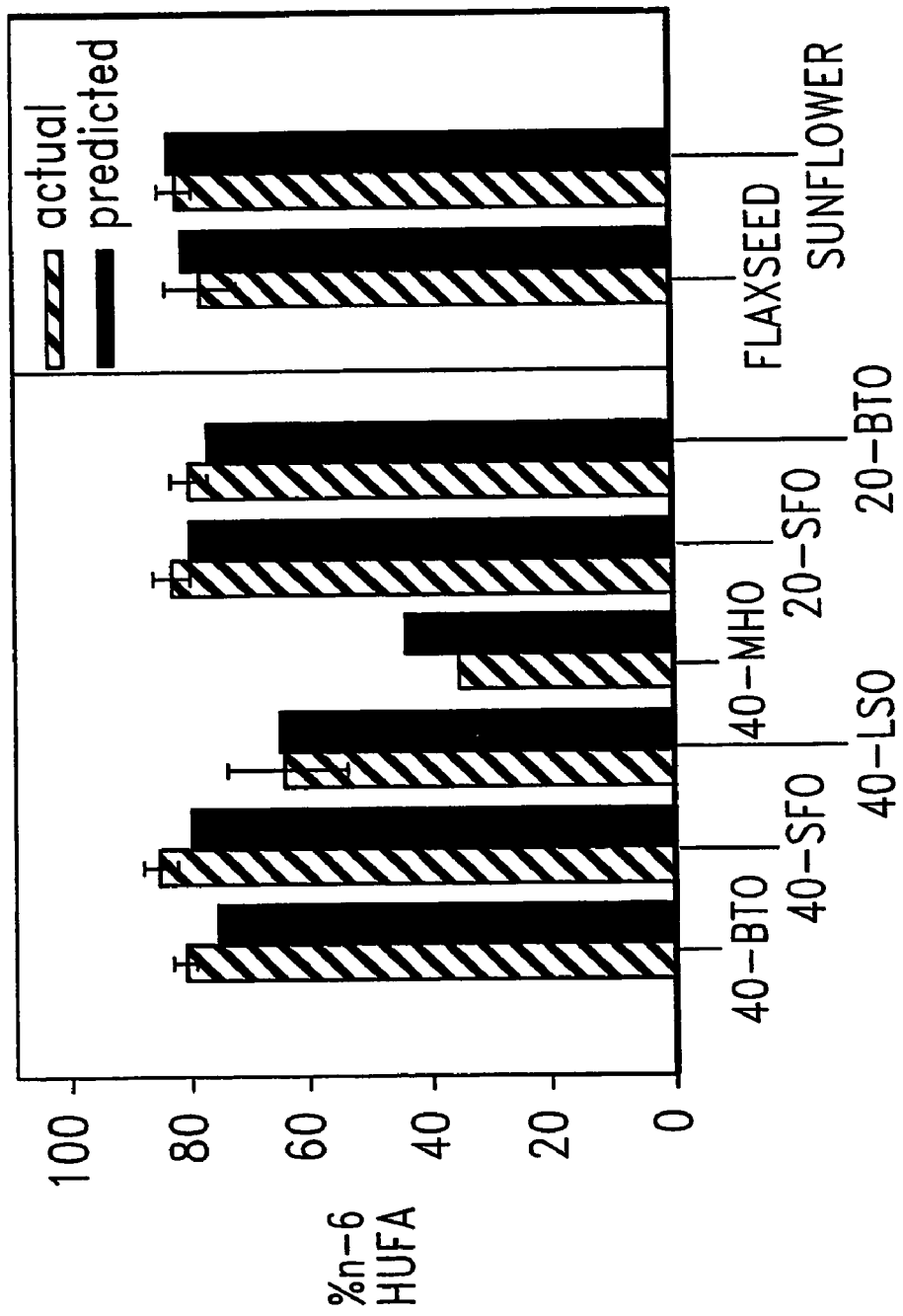
FIG. 4 is similar to FIG. 3, except comparing the predicted and actual values of n-6 HUFA enrichment in canine plasma.

FIGS. 1 (plasma) and 2 (neutrophils) show the predicted phospholipid and triglyceride levels for various diets. A comparison of the actual versus predicted values of % (n-6) HUFA and % (n-3) HUFA enrichment in canine plasma is shown in FIGS. 3 and 4. Six of the samples, 40-BTO (beef tallow supplemented, 40% energy), 40-SFO (safflower oil supplemented, 40% energy), 40-LSO (inseed oil supplemented, 40% energy), 40-MHO (menhaden fish oil supplemented, 40% energy), 20-SFO (safflower oil supplemented, 20% energy), and 20-BTO (beef tallow supplemented, 20% energy) were the samples used to derive the equations and the constants. The flaxseed (jbflax) and sunflower (jbsunf) enriched diets are independent examples demonstrating the accuracy of the predicted values.

A common way to test the effectiveness of a proposed diet formulation is to feed the proposed diet to a group of dogs for a period of time, perhaps 3-4 weeks or more, and subsequently measure the plasma and neutrophil levels of fatty acids and levels of enrichment If the measurements indicated that adjustments to the proposed diet were necessary, the adjusted proposed diet similarly may be fed to a group of dogs, to determine if the proper levels were reached. The above equations describe the saturation kinetics of plasma and neutrophils and can be used to formulate various canine diets that are both cost effective and achieve various desired effects. Such formulations may be derived without the need for experimental data obtained by feeding a proposed diet to the canine animals. With the present invention, a few calculations will reveal whether the diet achieves the desired result. If the diet does not achieve the desired result, additional diets may be formulated and tested using the methods of this invention.

EXAMPLE 1

It is known that n-6 fatty acids are more pro-inflammatory than other dietary fatty acids. It is known that dogs will readily convert linoleic acid (n-6) to arachidonic acid, a precursor to the pro-inflammatory compounds prostaglandin $E_2$ ($PGE_2$) and leukotriene $B_4$ ($LTB_4$). In animals suffering from diseases that involve an alteration of the inflammatory response, it is often desirable to reduce the levels of n-6 fatty acids in the plasma or neutrophils. Thus, a diet may be desired that reduces the plasma and/or neutrophil levels of n-6 fatty acids. Since n-3 and n-6 polyunsaturated fatty acids compete for displacement of endogenous fatty acids, a formulator may propose a diet that is enriched for n-3 fatty acids, while reducing the amount of n-6 fatty acids in the diet. In one embodiment the % (n-6)HUFA in plasma or neutrophils is no more than 75% of the total HUFA, in another embodiment the % (n-6)HUFA in plasma or neutrophils is no more than 65%, and in yet another embodiment the % (n-6)HUFA in plasma or neutrophils is no more than 50%. Such diets are shown in FIGS. 1 and 2 as 40-LSO and 40-MHO, with 40-MHO providing much lower levels of n-6 in both plasma and neutrophils.

The above method may be used to formulate diets for a wide variety of veterinary conditions, including diseases involving inflammatory response and other eicosanoid-related disorders, such as cardiovascular disease, osteo and rheumatoid arthritis, lupus, and other autoimmune diseases.

EXAMPLE 2

A growing and emerging area in fatty acid metabolism is the importance of DHA (22:6n-3) in neurological development Although the literature does not provide clear guidance, there is general agreement that providing a source of n-3 fatty acids during late gestation and in the post neonatal period is beneficial. For example the World Health Organization recommends 20 mg of DHA/day for the first year of life. The International Society for the Study of Fatty Acids and Lipids (ISSFAL) recommends that DHA should be provided 35-75 mg/Kg/day with a total n-3 intake of 70-150 mg/Kg/day, and that the total n-6 to n-3 fatty acid ratio in the diet should range from 5:1 to a maximum of 10:1, with the ratio of DHA to AA in the range of 1:1 to 1:3. The ratio of DHA to EPA should be 5:1 or higher. Further evidence of the importance of DHA is the approval of the FDA to include DHA in infant formulas. No prior work in canine metabolism has been performed to demonstrate the importance of DHA.

As shown below in Table 2, it has been found that if the levels of n-6 are limited to under 6%, and n-3 levels are limited to 3-4% (as with the high fish diet), the equations demonstrate that significant incorporation of n-3 HUFA can be achieved.

TABLE 2

Predicted Fatty Acid Levels in Plasma

|  | linseed | hi fish | lo fish | tallow |
|---|---|---|---|---|
| en%3 | 15.23 | 0.1 | 0.1 | 0.1 |
| en%6 | 5.7 | 5.7 | 5.7 | 5.7 |
| en%H3 | 0.1 | 3.2 | 1.5 | 0.1 |
| en%H6 | 0.1 | 0.2 | 0.2 | 0.4 |
| En%O | 10.87 | 22.8 | 24.5 | 27.7 |
| % (n-3)HUFA | 29.8 | 22.8 | 12.5 | 1.5 |
| % (n-6)HUFA | 66.5 | 71.1 | 76.8 | 86.6 |
| % other HUFA | 3.6 | 6.1 | 10.6 | 12.0 |
| plasma TG (LA) | 17.8 | 17.8 | 17.8 | 17.8 |
| plasma TG (ALA) | 14.1 | 0.1 | 0.1 | 0.1 |

EXAMPLE 3

In addition to formulating a feed using the equations of the present invention, the equations can be used to provide dietary formulations that optimize the effect of dietary supplements. For example, if a pet owner supplements a dog's diet with a dietary supplement containing EPA and DHA, good incorporation of these n-3 HUFAs can be achieved if a diet is selected in which the levels of (n-6) are limited to under 6%.

EXAMPLE 4

Diets beneficial for renal health may be formulated. It is known that n-3 fatty acids are "renoprotective." Brown, S A, et al., *J. Clin., Lab., Med,* 131:447-55 (1998). Thus, diets rich in n-3 fatty acids and low in n-6 fatty acids may be formulated for renal health.

EXAMPLE 5

Hypertension is a leading indicator of coronary vascular disease. The rise in systolic blood pressure and pulse pressure with aging is a consequence of arterial stiffness. Several factors have been shown to decrease arterial stiffness including aerobic exercise, decreased sodium intake, and n-3 fatty acids. Thus, diets could be formulated to be high in n-3 fatty acids, to decrease hypertension.

EXAMPLE 6

Diets to reduce the effects of hyperlipidemia may be formulated. Hyperlipidemia, high circulating cholesterol and triglycerides, is a leading indicator of heart disease in humans, and some canine breeds, including miniature Schnauzers, beagles, and terrier-type breeds, are predisposed to hyperlipidemia. Research in human nutrition has demonstrated that diets higher in polyunsaturated fatty acids (PUFA) are beneficial for the reduction of elevated cholesterol and triglycerides. Interestingly, higher PUFAs whether of the n-6 or n-3 families have a similar effect on the reduction of elevated cholesterol levels. However, only the n-3 fatty acids have an effect on the reduction of hypertriglyceridemia. Diets promoted by the American Heart Association, step I and step II, have recommendations for the amount of dietary PUFA. Diets may be formulated that contain specific amounts of PUFAs for the purpose of reducing hyperlipidemia If elevated cholesterol is the problem, diets high in n-3 and/or n-6 fatty acids may be provided. If triglyceride levels are elevated, diets high in n-3 fatty acids may be provided.

EXAMPLE 7

A dermatological inflammatory response is a type of autoimmune condition. Diets for autoimmune conditions having reduced levels of n-6 fatty acids, as discussed above in Example 1, would be beneficial for animals suffering from a dermatological condition that is due to an inflammatory response etiology. See Calder, P C et al, *J. Med. Biol. Res.,* 31(4):467-90 (1998).

EXAMPLE 8

Diets may be formulated for other dermatological conditions as well. Dermatological conditions that are not associated with an inflammatory response, such as eczema or psoriasis, may benefit from a diet that is very different from a diet given to a canine suffering from an autoimmune condition. It is known that linoleic acid (18:2n-6) is required for the maintenance of the epidermal water barrier in the skin. Thus, in normal animals supplementation with n-6 containing oils (vegetable oils) contributes to the elasticity of the skin and luster (shininess) of the coat. This is one reason why typical pet foods tend to be high linoleic acid. While many of the above diets suggest that n-6 fatty acids should be reduced in the treatment of specific conditions, various studies suggest that both n-6 and n-3 fatty acids are beneficial in the normal canine diet. For example, recent studies have shown that in the short term both n-3 (18:3n-3) and n-6 (18:2n-6) were beneficial in improving skin and coat in normal dogs. Diets for normal healthy dogs may be formulated to include higher levels of both n-3 and n-6 fatty acids, while diets for canines suffering from non-inflammatory dermatological conditions may be formulated to include higher levels of n-6 fatty acids.

EXAMPLE 9

The above equations may also be used to generate a more cost effective diet, while maintaining desired fatty acid levels. For example, if one wishes to enrich the levels of n-3 fatty acids, a formulator may design a diet having greater than 9 en % 3. However, using the above formulae, one can determine that similar levels of enrichment may be obtained using only 5-7 en % 3, as seen in Table 3 below. Note that changing the en % n-3 HUFA only changes the EPA and DPA from 30.4% of total HUFA to 37.9% of total HUFA.

TABLE 3

|  | Linseed | Hi fish | lo fish | tallow | Linseed b | Hi fish b | lo fish b | tallow b |
|---|---|---|---|---|---|---|---|---|
| en%3 | 15.23 | 0.1 | 0.1 | 0.1 | 15.23 | 0.1 | 0.1 | 0.1 |
| en%6 | 5.7 | 5.7 | 5.7 | 5.7 | 5.7 | 5.7 | 5.7 | 5.7 |
| en%H3 | 0.1 | 5 | 1.5 | 0.1 | 0.1 | 7 | 1.5 | 0.1 |
| en%H6 | 0.1 | 0.2 | 0.2 | 0.4 | 0.1 | 0.2 | 0.2 | 0.4 |
| en%O | 10.9 | 20 | 24.5 | 25.7 | 10.9 | 18 | 24.5 | 25.7 |
| EPA + DPA as % HUFA | 16.3 | 30.4 | 11.7 | 1.5 | 16.3 | 37.9 | 11.7 | 1.5 |
| DGLA + AA as % HUFA | 74.0 | 66.1 | 76.9 | 86.6 | 74.0 | 61.1 | 76.9 | 86.6 |
| DHA + 20:3n–9 as % HUFA | 9.8 | 3.6 | 11.4 | 12.0 | 9.8 | 0.9 | 11.4 | 12.0 |

Thus, the formulae of the present invention may be used develop a less expensive diet that achieves essentially the same result with respect to fatty acid levels.

EXAMPLE 10

The above equations may be used to confirm compliance with a prescribed diet. The diet may be formulated to achieve desired n-3 and/or n-6 fatty acid levels, and predicted triglyceride and/or phospholipid levels may be calculated using the equations of this invention. A veterinarian may prescribe the diet to a particular canine animal to treat a specific condition, or the diet may be prescribed as part of clinical trials. Subsequently, after a sufficient period of time has passed, a blood sample may be drawn from the canine and the actual fatty acid levels would be compared to the predicted levels to determine compliance with the diet Preferably, these values should be within 10% of the standard error of the mean, and more preferably within 5% of the standard error of the mean. However, it is understood that the actual values may vary more or less, depending on the application.

The foregoing discussion discloses and describes merely exemplary embodiments of the present invention. One skilled in the art will readily recognize from such discussion, and from the accompanying drawings and claims, that various changes, modifications and variations can be made therein without departing from the spirit and scope of the invention as defined in the following claims.

All references cited herein are incorporated by reference as if fully set forth.

The invention claimed is:

1. A computer implemented method for providing nutrition to a canine achieved by feeding a proposed diet of a predetermined fatty acid composition including values for en % 3, en % 6, en % O, en % $H_6$ and en % $H_3$, comprising the steps of calculating for the proposed diet, a predicted n-6 phospholipid fatty acid level as a percentage of total HUFA by a computer processor configured to determine the predicted n-6 phospholipid fatty acid level, wherein $$\% (n\text{-}6)HUFA = 100/1 + \{(PC_6/en\ \%\ 6)[1+ (en\ \%\ 3/KI_3) + (en\ \%\ H_3/HI_3) + (en\ \%\ )/C_O) + (en\ \%\ 6/K_s)]\} + 100/1 + \{(HC_6/en\ \%\ H_6)[1+ (en\ \%\ H_3/HC_3)]\}$$

wherein en % 3 is a percent daily energy of α-linolenic acid,
en % 6 is a percent daily energy of linoleic acid,
en % O is a percent daily energy of other fatty acids,
en % $H_6$ is a percent daily energy of n-6 HUFA,
en % $H_3$ is a percent daily energy of n-3 HUFA,
$PC_6$=0.036,
$C_O$=9.00,
$K_s$=0.140,
$HI_3$=0.100,
$HC_6$=4.00,
$HC_3$=11.00,
$KI_6$=0.72 when the tissue is plasma and 0.034 when the tissue is neutrophils and
$K1_3$=0.34 when the tissue is plasma and 0.80 when the tissue is, neutrophils;
comparing the predicted %(n-6)HUFA to a predetermined level;
determining the proposed diet to be acceptable if the predicted %(n-6)HUFA does not exceed the predetermined level; formulating the acceptable proposed diet; and
administering the proposed diet to the canine.

2. The method of claim 1, wherein the step of the step of calculating further comprises:

$$\% (n\text{-}3)HUFA = 100/1 + \{(PC_3/en\ \%\ 3)[1+(en\ \%\ 6/KI_6) + (en\ \%\ H_6/HI_6) + (en\ \%\ O/C_O) + (en\ \%\ 3/K_s)]\} + 100/1 + \{(HC_3/en\ \%\ H_3)[1+(en\ \%\ H_6/HC_6)]\}$$

wherein $PC_3$=0.290, and
$HI_6$=0.010;
the step of comparing further comprises comparing the predicted % (n-3)HUFA to a predetermined level;
and the step of determining further comprises determining the proposed diet to be acceptable if the predicted % (n-3)HUFA does not exceed the predetermined level; and.

3. The method of claim 2, wherein the tissue is plasma.

4. The method of claim 2, wherein the tissue is neutrophils.

5. The method of claim 1, wherein the predetermined level is 75% and the tissue is plasma.

6. The method of claim 1, wherein the predetermined level is 65% and the tissue is plasma.

7. The method of claim 1, wherein the predetermined level is 50% and the tissue is plasma.

8. The method of claim 1, wherein if the predicted % (n-6) HUFA is greater than the predetermined level, the method comprises the steps of altering the proposed diets, and repeating the % (n-6)HUFA calculating step to obtain a new predicted % (n-6)HUFA value.

9. The method of claim 8, wherein the altering and repeating steps are repeated until a predicted new % (n-6)HUFA is obtained that is not greater than the predetermined level.

10. A computer implemented method for providing nutrition to a canine achieved by feeding a proposed diet of a predetermined fatty acid composition including values for en % 3, en % 6, en % O, en % $H_6$ and en % $H_3$, comprising the steps of calculating for the proposed diet, a predicted n-3 phospholipid fatty acid level as a percentage of total HUFA by a computer processor configured to calculate the predicted n-3 phospholipid fatty acid level, wherein $$\% \ (n\text{-}3)HUFA = 100/1 + \{(PC_3/en \% \ 3)[1 + (en \% \ 6/KI_6) + (en \% \ H_6/HI_6) + (en \% \ O/C_O) + (en \% \ 3/K_s)]\} + 100/1 + \{(HC_3/en \% \ H_3)[1 + (en \% \ H_6/HC_6)]\}$$

wherein en % 3 is a percent daily energy of α-linolenic acid,
en % 6 is a percent daily energy of linoleic acid,
en % O is a percent daily energy of other fatty acids, e
n % $H_6$ is a percent daily energy of n-6 HUFA,
en % $H_3$ is a percent daily energy of n-3 HUFA,
$PC_3$=0.290,
$C_O$=9.00,
$K_s$=0.140,
$HI_6$=0.010,
$HC_6$=4.00,
$HC_3$=11.00,
$KI_6$=0.72 when the tissue is plasma and 0.034 when the tissue is neutrophils, and
$KI_3$=0.34 when the tissue is plasma and 0.80 when the tissue is neutrophils;
comparing the predicted %(n-3)HUFA to a predetermined level;
determining the proposed diet to be acceptable if the predicted %(n-3)HUFA exceeds the predetermined level;
formulating the acceptable proposed diet; and
administering the proposed diet to the canine.

11. The method of claim 10, wherein the predetermined level is 20% and the tissue is plasma.

12. A computer implemented method for providing nutrition to a canine comprising the steps of:
(a) determining a percent caloric daily energy of linoleic acid in a diet;
(b) calculating for the proposed diet a predicted percent enrichment by an equation $y=-0.62x^2+2.75x+4.04$ wherein y is a percent enrichment and x is a percent caloric daily energy of linoleic acid in a diet by a computer processor configured to determine the predicted percent enrichment; formulating the acceptable proposed diet; and
(c) administering the diet to the canine.

13. A computer implemented method for providing nutrition to a canine comprising the steps of:
(a) determining a percent caloric daily energy of α-linolenic acid in a diet;
(b) calculating for the proposed diet a predicted percent enrichment by an equation $y=-0.012x^2+1.11x+0.02$ wherein y is a percent enrichment and x is a percent caloric daily energy of α-linolenic acid in a diet by a computer processor configured to determine the predicted percent enrichment; formulating the acceptable proposed diet; and
(c) administering the diet to the canine.

14. A computer implemented method for determining compliance with a prescribed diet for an individual canine animal, the prescribed diet having a predetermined fatty acid composition, comprising the steps of
determining an expected fatty acid level for the prescribed diet selected from the group consisting of: an expected n-6 phospholipid fatty acid level as a percentage of total HUFA (% (n-6) HUFA), an expected n-3 phospholipid fatty acid level as a percentage of total HUFA (% (n-3) HUFA), an expected percent enrichment of α-linolenic acid in plasma triglycerides, and an expected percent enrichment of linoleic acid in plasma triglycerides by a computer processor configured to determine the expected fatty acid level, wherein the expected % $(n\text{-}6)HUFA = 100/1 + \{(PC_6/en \% \ 6)[1 + (en \% \ 3/KI_3) + (en \% \ H_3/HI_3) + (en \% \ O/C_O) + (en \% \ 6/K_s)]\} + 100/1 + \{(HC_6/en \% \ H_6)[1 + (en \% \ H_3/HC_3)]\}$ the expected % $(n\text{-}3)HUFA = 100/1 + \{(PC_3/en \% \ 3)[1 + (en \% \ 6/KI_6) + (en \% \ H_6/HI_6) + (en \% \ O/C_O) + (en \% \ 3/K_s)]\} + 100/1 + \{(HC_3/en \% \ H_3)[1 + (en \% \ H_6/HC_6)]\}$ the expected percent enrichment of α-linolenic acid in plasma triglycerides=$-0.012x^2+1.11x+0.02$,
the expected percent enrichment of linoleic acid in plasma triglycerides=$-0.62z^2+2.75z+4.04$,
en % 3 is a percent daily energy of α-linolenic acid,
en % 6 is a percent daily energy of linoleic acid,
en % O is a percent daily energy of other fatty acids,
en % $H_6$ is a percent daily energy of n-6 HUFA,
en % $H_3$ is a percent daily energy of n-3 HUFA,
$PC_3$=0.036,
$C_O$=9.00,
$K_s$=0.140,
$HI_3$=0.100,
$HC_6$=4.00,
$HC_3$=11.00,
$KI_6$=0.72 when the tissue is plasma and 0.034 when the tissue is neutrophils,
$KI_3$=0.34 when the tissue is plasma and 0.80 when the tissue is neutrophils,
x is a percent caloric daily energy of α-linolenic acid in a diet, and
z is a percent caloric daily energy of linoleic acid in a diet,
obtaining a blood sample from the canine animal,
measuring an actual fatty acid level corresponding to the predicted fatty acid level, and
comparing the actual fatty acid level to expected fatty acid level.

15. The method of claim 14, comprising the step of finding compliance when the actual fatty acid level is within 5% of a standard error of the mean.

\* \* \* \* \*

UNITED STATES PATENT AND TRADEMARK OFFICE
CERTIFICATE OF CORRECTION

PATENT NO. : 8,311,746 B2
APPLICATION NO. : 10/513550
DATED : November 13, 2012
INVENTOR(S) : John E. Bauer and Mark K. Waldron It is certified that error appears in the above-identified patent and that said Letters Patent is hereby corrected as shown below:

Title Page, Col. 2, line 4,
  [56] References cited:  "9n-60" should read -- (n-6) --;

In the Drawings:
 Figure 3: "%n-3 HUFA" should read -- Relative % n-3 HUFA --;

Figure 4: "%n-6 HUFA" should read -- Relative % n-6 HUFA --;

In the Specification:
 Column 1, line 29: "(20:3n9 and 20:4n-7 types)" should read -- (20:3n-9 and 20:4n-7 types) --;

Column 2, line 13: "a-linolenic" should read -- α-linolenic --;

Column 2, line 29: "en%6" should read -- en % n-6 --;

Column 2, line 29: "en % 6" should read -- en % n-6 --;

Column 2, line 35: "en % 3" should read -- en % n-3 --;

Column 3, line 8: "n-3 HUFA" should read -- relative n-3 HUFA --;

Column 3, line 12: "n-6 HUFA" should read -- relative n-6 HUFA --;

Column 4, line 18: "(en % 6)" should read -- (en % n-6) --;

Column 4, line 26: "(en % 3)" should read -- (en % n-3) --;

Column 4, line 63: "en % 3" should read -- en % n-3 --;

Column 4, line 63: "en % 6" should read -- en % n-6 --;

Column 4, line 63: "H6" should read – $H_6$ –;

Signed and Sealed this
Twenty-fourth Day of September, 2013

Teresa Stanek Rea
*Deputy Director of the United States Patent and Trademark Office*

CERTIFICATE OF CORRECTION (continued)
U.S. Pat. No. 8,311,746 B2

Column 5, line 39: "ALA." should read -- ALA, respectively. --;

Column 5, line 58: "% (n-6) HUFA" should read -- relative % (n-6) HUFA --;

Column 5, line 59: "% (n-3) HUFA" should read -- relative % (n-3) HUFA --;

Column 6, line 49: "% (n-6)HUFA" should read -- % (n-6) HUFA --;

Column 6, line 51: "% (n-6)HUFA" should read -- % (n-6) HUFA --;

Column 6, line 52: "% (n-6)HUFA" should read -- % (n-6) HUFA --;

Column 6, line 67: "development Although" should read -- development. Although --;

Column 7, line 15: "6%" should read -- 6 en % --;

Column 7, line 16: "3-4%" should read -- 3-4 en % --;

Table 2 (col 7, ln 25): "en%3" should read -- en % n-3 --;

Table 2 (col 7, ln 26): "en%6" should read -- en % n-6 --;

Table 2 (col 7, ln 27): "en%H3" should read -- en % H3 --;

Table 2 (col 7, ln 27): "en%H6" should read -- en % H6 --;

Table 2 (col 7, ln 28): "% (n-3)HUFA" should read -- Relative % (n-3) HUFA --;

Table 2 (col 7, ln 29): "% (n-6)HUFA" should read -- Relative % (n-6) HUFA --;

Table 2 (col 7, ln 30): "% other HUFA" should read -- Relative % other HUFA --;

Column 7, line 44: "6%" should read -- 6 en % --;

Column 8, line 63: "9 en % 3" should read -- 9 en % n-3 --;

Column 8, line 65: "5-7 en %3" should read -- 5.7 en % n-3 --;

Table 3 [Title none]: Title should read -- Effect of H3 on EPA and DHA as a % of total plasma HUFA --

Table 3 (col 9, ln1-10): "en%3" should read -- en % n-3 --;

Table 3 (col 9, ln1-10): "en%6" should read -- en % n-6 --;

Table 3 (col 9, ln1-10): "en%H3" should read -- en % H3 --;

Table 3 (col 9, ln1-10): "en%H6" should read -- en % H6 --;

In the Claims:

Claim 1 (col 9, ln 49): "en % 3" should read -- en % n-3 --;

Claim 1 (col 9, ln 50): "en % 6" should read -- en % n-6 --;

Claim 1 (col 9, ln 60): "en % 3" should read -- en % n-3 --;

CERTIFICATE OF CORRECTION (continued)
U.S. Pat. No. 8,311,746 B2

Claim 1 (col 9, ln 62): "en % 6" should read -- en % n-6 --;

Claim 1 (col 10, ln 24): "%(n-6)HUFA" should read -- % (n-6) HUFA --;

Claim 1 (col 10, ln 27): "%(n-6)HUFA" should read -- % (n-6) HUFA --;

Claim 2 (Col 10, ln 40): "% (n-3)HUFA" should read -- % (n-3) HUFA --;

Claim 2 (col 10, ln 43): "% (n-3)HUFA" should read -- % (n-3) HUFA --;

Claim 8 (col 10, ln 56): "% (n-6)HUFA" should read -- % (n-6) HUFA --;

Claim 8 (col 10, ln 57): "% (n-6)HUFA" should read -- % (n-6) HUFA --;

Claim 10 (col 10, ln 63-64): "en % 3" should read -- en % n-3 --;

Claim 10 (col 10, ln 64): "en % 6" should read -- en % n-6 --;

Claim 10 (col 11, ln 8): "en % 3" should read -- en % n-3 --;

Claim 10 (col 11, ln 10): "en % 6" should read -- en % n-6 --;

Claim 10 (col 11, ln 24): "%(n-3)HUFA" should read -- % (n-3) HUFA --;

Claim 10 (col 11, ln 27): "%(n-3)HUFA" should read -- % (n-3) HUFA --;

Claim 14 (col 12, ln 27): "en % 3" should read -- en % n-3 --;

Claim 14 (col 12, ln 28): "en % 6" should read -- en % n-6 --;